United States Patent [19]

Pirie et al.

[11] Patent Number: 4,499,017
[45] Date of Patent: Feb. 12, 1985

[54] BETA-LACTAMASE INHIBITING 6-(ALKOXYAMINO-METHYL) PENICILLANIC ACID 1,1-DIOXIDE AND DERIVATIVES

[75] Inventors: Donald K. Pirie, Uncasville; Robert A. Volkmann, Ledyard; Edward F. Kleinman, Groton, all of Conn.

[73] Assignee: Pfizer Inc., New York, N.Y.

[21] Appl. No.: 501,475

[22] Filed: Jun. 6, 1983

[51] Int. Cl.³ ................ C07D 499/00; A61K 31/415
[52] U.S. Cl. ...................... 260/245.2 R; 260/245.2 T
[58] Field of Search ................. 260/245.2 R; 424/270

[56] References Cited

U.S. PATENT DOCUMENTS 4,234,579 3/1979 Barth .................................. 424/246
4,287,181 9/1981 Kellogg ........................ 424/271 X Primary Examiner—Nicholas S. Rizzo
Attorney, Agent, or Firm—Charles J. Knuth; Albert E. Frost; Robert K. Blackwood

[57] ABSTRACT 6-alpha/beta-[($C_1$–$C_4$)Alkoxyaminomethyl and benzyloxyaminomethyl]penicillanic acid 1,1-dioxides, pharmaceutically acceptable salts thereof and conventional esters thereof hydrolyzable under physiological conditions, all of which are useful in medicine as beta-lactamase inhibitors; intermediates and processes therefor; and a process for the conversion of the present compounds to 6-alpha- and 6-beta-(aminomethyl)-penicillanic acid 1,1-dioxides and derivatives.

28 Claims, No Drawings

BETA-LACTAMASE INHIBITING 6-(ALKOXYAMINO-METHYL) PENICILLANIC ACID 1,1-DIOXIDE AND DERIVATIVES

BACKGROUND OF THE INVENTION

The present invention is concerned with 6-alpha- and 6-beta-[($C_1$–$C_4$)alkoxyaminomethyl and benzyloxyaminomethyl]penicillanic acid 1,1-dioxides, pharmacuetically acceptable salts thereof and conventional esters thereof hydrolyzable under physiological conditions, all of which are useful in medicine as beta-lactamase inhibitors; intermediates and processes therefor; and a process for the conversion of various of the present compounds to 6-alpha- and 6-beta-(aminomethyl)-penicillanic acid 1,1-dioxides and derivatives.

beta-Lactamase inhibitors represent an important class of medicinal agents, useful in combination with conventional beta-lactam antibiotics (penicillins and cephalosporins) against microorganisms resistant or partially resistant to those antibiotics through production of beta-lactamase enzymes.

Compounds (and corresponding hydrolyzable esters) which are known to possess desirable beta-lactamase inhibitory activity include penicillanic acid 1,1-dioxide (Barth, U.S. Pat. No. 4,234,579), various 6-beta-(hydroxymethyl)penicillanic 1,1-dioxides (Kellogg, U.S. Pat. No. 4,287,181), 6-alpha- and 6-beta-(benzylaminomethyl)penicillanic acid 1,1-dioxides (copending Barth, U.S. Ser. No. 388,323, filed June 14, 1982) and 6-alpha- and 6-beta-(aminomethyl)penicillanic acid 1,1-dioxides (copending Barth, U.S. Ser. No. 434,371, filed Oct. 21, 1982). Indeed, the compounds of the present invention find further utility as intermediates in an improved synthesis of said aminomethyl compounds of Barth.

The Grignard reagents derived from 6-alpha-bromopenicillanate 1,1-dioxide esters which are employed in the present invention are one of the objects of concurrently filed U.S. application, Ser. No. 501,476 for "Process for 6-(Aminomethyl)penicillanic Acid 1,1-Dioxide and Derivatives Thereof," by Barth.

SUMMARY OF THE INVENTION

The present invention is concerned with compounds having the formula

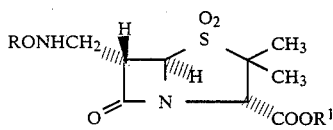

or

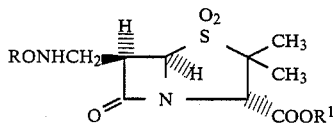

wherein R is ($C_1$–$C_4$)alkyl or benzyl; and $R^1$ is hydrogen or a conventional ester forming radical which is hydrolyzable under physiological conditions; and the pharmaceutically acceptable cationic salts thereof when $R^1$ is hydrogen.

Pharmaceutically-acceptable cationic salts include, but are not limited to, those of sodium, potassium, calcium, N,N'-dibenzylethylenediamine, N-methylglucamine (meglumine) and diethanolamine. The reference to esters which are hydrolyzable under physiological conditions is directed to those esters frequently referred to as "pro-drugs". Such esters are now as well-known and common in the penicillin art as pharmaceutically-acceptable salts. Such esters are generally used to enhance oral absorption, but in any event are readily hydrolyzed in vivo to the parent acid, having beta-lactamase inhibitory activity. The preferred ester forming radicals are:

gamma-butyrolacton-4-yl,
—$CHR^2OCOR^3$, and
—$CHR^2OCOOR^3$, wherein $R^2$ is hydrogen or methyl and $R^3$ is ($C_1$–$C_6$)alkyl. The most preferred radicals are pivaloyloxymethyl and 1-ethoxycarbonyloxyethyl.

For use in therapy in combination with beta-lactam antibiotics, the preferred values of R are methyl and ethyl. For use as intermediates in the synthesis of corresponding alpha- and beta-(aminomethyl)penicillanic acid 1,1-dioxides, the preferred values of R are methyl, ethyl and benzyl; and preferred hydrolyzable ester groups are not hydrogenolyzable under the conditions presently used for their preparation.

The present invention is also concerned with intermediate compounds having the formula

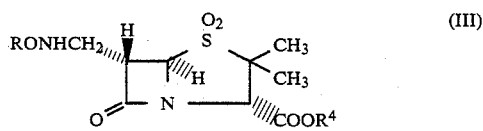

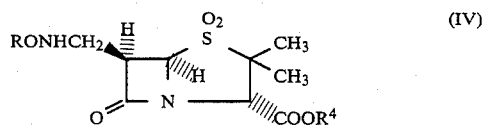

or

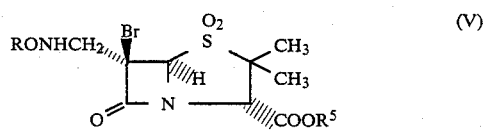

wherein R is ($C_1$–$C_4$)alkyl or benzyl; $R^4$ is a conventional carboxy protecting group removable by hydrogenolysis; and $R^5$ is $R^4$ or a conventional ester forming radical which is hydrolyzable under physiological conditions.

Conventional carboxy protecting groups removable by hydrogenolysis are also very common in the penicillin art. In the present instance, benzyl, benzydryl and 2-naphthylmethyl are preferred examples of such groups, but the invention should not be so construed as limited to these three hydrogenolyzable groups. Preferred physiologically hydrolyzable groups are as detailed above. For use in the preparation of the present therapeutic compounds (I) and (II), the preferred values of R are methyl and ethyl. For use in the preparation of corresponding aminomethyl derivatives, the preferred values of R are methyl, ethyl and benzyl.

The present invention also encompasses a process for the preparation of (a) a compound of the formula

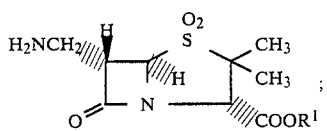

(b) a compound of the formula

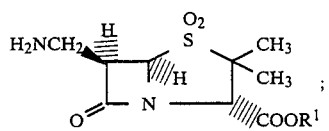

or (c) a mixture of the compounds of the formulae (VI) and (VII);

wherein in said formulae (VI) and (VII), $R^1$ is as defined above; which comprises hydrogenation over a Raney nickel catalyst of:

(A) when $R^1$ is hydrogen, respectively,
(a) a compound of the formula

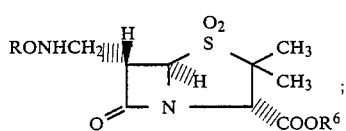

(b) a compound of the formula

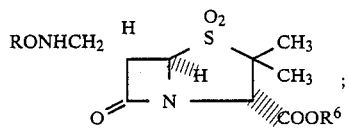

(c) a mixture of the compounds of the formulae (VIII) and (IX), or a compound of the formula

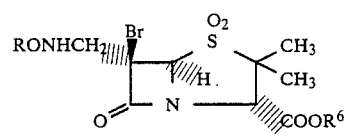

wherein, in said formulae (VIII), (XI) and (X), R is as defined above and $R^6$ is hydrogen or a conventional carboxy protecting group removable by hydrogenolysis; or (B) when $R^1$ is said ester forming radical which is hydrolyzable under physiological conditions, respectively,
(a) a compound of the formula

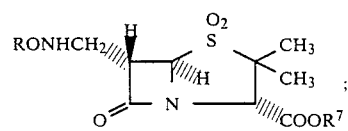

(b) a compound of the formula

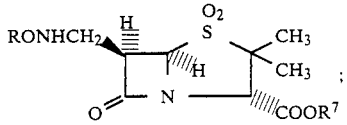

or (c) a mixture of the compounds of the formulae (XI) and (XII), or a compound of the formula

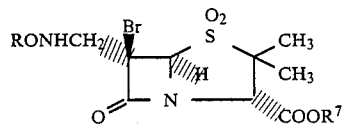

wherein, in said formulae (XI), (XII) and (XIII), R is as defined above and $R^7$ is a conventional ester forming radical which is hydrolyzable under physiological conditions.

The present invention further comprises a process for the preparation of a compound of the formula

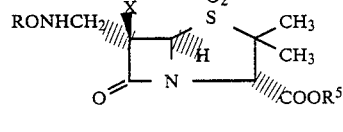

wherein $R^5$ is as defined above; X is hydrogen or bromo; and R is as defined above; which comprises:
reacting a compound of the formula

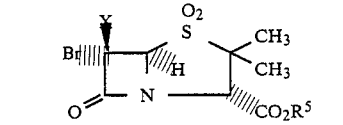

wherein $R^5$ and X are as defined above; with substantially one equivalent of methylmagnesium bromide or chloride in an ethereal solvent at $-50°$ to $-100°$ C.; and reacting the resulting solution at $-50°$ to $-100°$ C. with substantially one equivalent each of RO—N=$CH_2$ (wherein R is as defined above) and $BF_3$, optionally predissolved in an ethereal solvent and precooled to $-50°$ to $-100°$ C.

$BF_3$, being used in an ethereal solvent, is conveniently introduced in the form of its ether complex ($BF_3$.etherate).

DETAILED DESCRIPTION OF THE INVENTION

When $R^1$ is hydrogen and R is other than benzyl, the compounds of the formula (I) or (II), or a mixture thereof, are readily prepared by the noble metal catalyzed hydrogenolysis of the corresponding compounds (III) or (IV), or a mixture thereof or a compound of the formula (V) wherein $R^5$ is removable by hydrogenolysis. Said hydrogenolysis is carried out under mild conditions by methods well-known in the penicillin art. The substrate, in a reaction-inert solvent, is contacted with hydrogen in the presence of a noble metal catalyst, such as palladium, platinum or rhodium, optionally in the form of its oxide or a salt, or on a carrier such as carbon, an alkaline earth carbonate or alumina. Temperature is not critical (e.g. 0°–50° C.), but is preferably 25° C. or lower in order to minimize thermal degradation. Pressure can be varied over a wide range (subatmospheric to 100 atmospheres), but as a matter of preference as well as convenience will generally be in the range of 1 to 7 atmospheres. The reaction inert solvent is preferably relatively low boiling so as to be readily removed by concentration in vacuo. As used herein the expression "reaction-inert solvent" defines a solvent which does not interact with starting materials, reagents, intermediates or products in a manner which significantly reduces the yield of the desired product. Aqueous tetrahydrofuran is a solvent particularly well-suited for the present purpose. The preferred catalyst is palladium, supported on carbon.

When $R^1$ is hydrogen and R is benzyl, it is preferable to prepare the compounds of the formula (I) or (II), or a mixture thereof, by mild, laboratory hydrolysis of the corresponding compound of the formula (I) or (II), or mixture of (I) and (II), wherein $R^1$ is an ester forming radical hydrolyzable under physiological conditions. Said laboratory hydrolysis is carried out in an aqueous solvent under mild conditions (e.g. at a pH in the range 8–10 at 0°–30° C.) in order to minimize degradation reactions.

Compounds of the formula (I) when $R^1$ is other than hydrogen, or of the formula (III) or (V), which are alternatively defined above as compounds of the formula (XIV), are prepared from corresponding compounds of the formula (XV) by first reacting the latter with substantially one equivalent of a simple Grignard reagent such as methylmagnesium bromide or chloride at $-50°$ to $-100°$ C. in an etheral solvent such as tetrahydrofuran, forming the C-6 Grignard reagent with retention of stereochemistry. The resulting solution is then reacted (immediately or within 60 minutes), in the same temperature range, with substantially one equivalent each of $RO-N=CH_2$ (wherein R is as defined above) and $BF_3$, optionally precombined as a second solution in an ethereal (usually the same) solvent at $-50°$ to $-100°$ C.

The 6-alpha compounds of the formula (I) or (III) are alternatively prepared from the corresponding 6-beta compounds of the formula (II) or (IV) by contacting the latter with 1,5-diazabicyclo[4.3.0]-non-5-ene, usually substantially one equivalent, in a reaction inert solvent such as methylene chloride at about 0°–50° C., conveniently at ambient temperature.

The 6-beta compounds of the formula (II) or (IV) are prepared by the tri-n-butyltin hydride reduction of the corresponding 6-beta-bromo compound (V) [also defined above as compound (XIV) wherein X is bromo]. This reduction is generally carried out with an excess of the hydride (e.g. 2—4 equivalents) in a reaction inert solvent such as benzene at 50°–100° C., conveniently at the reflux temperature of benzene. A 6-alpha-bromo epimer of the compound (V) will also yield the present 6-beta compounds (II) and (IV) under the conditions of the present tri-n-butyltin hydride reduction.

The present starting material esters are prepared from the mono- or dibromo penicillanic acids by the methods which are standard in the penicillin art, e.g., by reaction of the salt of an acid of the formula

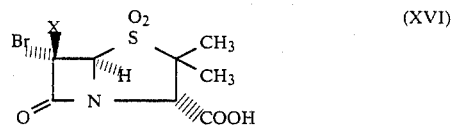

wherein X is as defined above with a compound $R^5Q$ where $R^5$ is as defined above and Q is a leaving group such as a halide or sulfonate ester. Exemplary of such compounds are chloromethyl pivalate, bromomethyl acetate, 1-ethoxycarbonyloxyethyl chloride, 1,3-dihydro-3-oxobenzo[c]furan-1-yl bromide, benzyl chloride, benzyl bromide, benzyl mesylate, 2-bromomethylnaphthalene and benzhydryl chloride. The acid salt can be preformed, or formed in situ. Examples are triethylamine salts, sodium salts and preferred tetrabutylammonium salts.

6-alpha-Bromopenicillanic acid 1,1-dioxide and derivatives are preferably obtained by novel sodium bisulfite reduction of 6,6-dibromopenicillanic acid 1,1-dioxide and its derivatives. This process, which is exemplified below, is the subject of concurrently filed U.S. Patent application Ser. No. 501,731 for "Process for Debromination of Dibromopenicillanic Acid and Derivatives" by Pirie and Weeks.

The above-defined pharmaceutically-acceptable cationic salts of those compounds of the present invention having a free carboxylic acid group are also readily prepared by standard methods. For example, an equivalent of the corresponding cationic hydroxide, carbonate or bicarbonate or of an amine is combined with the carboxylic acid in an organic or aqueous solvent, preferably at reduced temperature (e.g. 0°–5° C.), with vigorous agitation and slow addition of the base. The salt is isolated by concentration and/or the addition of a nonsolvent. If desired, these methods are used to isolate the salt directly from reaction mixtures, without prior isolation of the free acid form.

As noted above, present compounds (I), (II), (III), (IV) and (V), and mixtures (I and II) and (III and IV) [also appropriately redefined above as compounds (VIII), (IX), (X), (XI), (XII) and (XIII), and mixtures (VIII and IX) and (XI and XII)] are variously useful as substrates for Raney nickel catalyzed hydrogenation to 6-aminomethyl compounds of the formula (VI) and (VII), and mixtures thereof. Such hydrogenations are carried out under conditions (temperatures, pressures, solvents) as described above, except that Raney nickel catalyst is used in place of the noble metal catalyst. Raney nickel catalysts of various activity are available commercially or according to methods well documented in the literature. Preferred for the present use are Raney nickel catalyst of higher designated activity, e.g. W-5 to W-7 (for references, see House, "Modern Synthetic Reactions", 2nd Edition, 1972, page 6); or commercial Raney nickel preparations such as that designated as nos. 2400, 2800 or 3200 by Davison Specialty Chemical Co. (Division of W. R. Grace and Company), Baltimore, Maryland; or molybdenum promoted Raney nickel of DeGussa Corp., Metal and Catalyst Division, Peterborough, N.J. The suitability of any particular type of Raney nickel in the present invention is readily determined by simple experiment.

As also indicated above, the compounds (I) and (II), and mixtures thereof, are of value as inhibitors of microbial beta-lactamases. By this mechanism they increase the antibacterial effectiveness of beta-lactam antibiotics (penicillins and cephalosporins) against many microorganisms, which are resistant or partially resistant to said antibiotic by producing a beta-lactamase. The ability of the said compounds of the formula (I) or (II) to increase the effectiveness of a beta-lactam antibiotic can be appreciated by reference to experiments in which the MIC values of the antibiotic alone, and a compound of the formula (I) or (II) (having $R^1$ as hydrogen) alone, are determined. These MIC's are then compared with the MIC values obtained with a combination of the given antibiotic and the compound of the formula (I) or (II), wherein $R^1$ is hydrogen. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd Edition, 1974, American Society for Microbiology.

The compounds of the formulae (I) and (II) also enhance the antibacterial effectiveness of the beta-lactam antibiotics in vivo, the esters functioning by hydrolysis to the fully active acids under such physiological conditions. The ability of the compounds of formulae (I) and (II) to enhance the effectiveness of a beta-lactam antibiotic against beta-lactamase producing bacteria makes them valuable for coadministration with beta-lactam antibiotics in the treatment of bacterial infections in mammals, particularly man. In the treatment of a bacterial infection, the compound of the formula (I) or (II) can be comingled with the beta-lactam antibiotic, and the two agents thereby administered simultaneously. Alternatively, the compound of the formula (I) or (II) can be administered as a separate agent during a course of treatment with a beta-lactam antibiotic. In some instances it will be advantageous to pre-dose the subject with the compound of the formula (I) or (II) before initiating treatment with a beta-lactam antibiotic.

When using a compound of formula (I) or (II) to enhance the effectiveness of beta-lactam antibiotic, a mixture of (I) or (II) with the beta-lactam antibiotic is administered preferably in formulation with standard pharmaceutical carriers or diluents. A pharmaceutical composition comprising a pharmaceutically acceptable carrier, a beta-lactam antibiotic and a compound of formula (I) or (II) will normally contain from about 5 to about 80 percent of the pharmaceutically acceptable carrier by weight.

When using the compounds of formula (I) or (II) in combination with another beta-lactam antibiotic, said compounds can be administered orally or parenterally, i.e. intramuscularly, subcutaneously or intraperitoneally. Although the prescribing physician will ultimately decide the dosage to be used in a human subject, the ratio of the daily dosages of the compounds of formula (I) or (II) and the beta-lactam antibiotic will nornally be in the range from about 1:3 to 3:1 by weight. Additionally, when using the compounds of formula (I) or (II) in combination with another beta-lactam antibiotic, the daily oral dosage of each component will normally be in the range from about 10 to about 200 mg per kilogram of body weight and the daily parenteral dosage of each component will normally be about 10 to about 40 mg per kilogram of body weight. These daily doses will usually be divided. In some instances, the prescribing physician will determine that dosages outside these limits are necessary.

As will be appreciated by one skilled in the art, some beta-lactam compounds are effective when administered orally or parenterally, while others are effective only when administered by the parenteral route. When a compound of formula (I) or (II) is to be used simultaneously (i.e comingled) with a beta-lactam antibiotic which is effective only on parenteral administration, a combination formulation suitable for parenteral use will be required. When a compound of formula (I) or (II) is to be used simultaneously (comingled) with a beta-lactam antibiotic which is effective orally or parenterally, combinations suitable for either oral or parenteral administration can be prepared. Additionally, it is possible to administer preparations of the compounds of formula (I) or (II) orally, while at the same time administering a further beta-lactam antibiotic parenterally; and it is also possible to administer preparations of the compounds of formula (I) or (II) parenterally, while at the same time administering the further beta-lactam antibiotic orally.

The compounds (VI) and (VII), derived from compounds of the present invention, are utilized in a manner identical to that of the compounds (I) and (II).

The present invention is illustrated by the following examples. However, it should be understood that the invention is not limited to the specific details of these examples. Unless otherwise specified, all operations were carried out at ambient temperatures; all temperature are in °C., all drying of solutions was over anhydrous $Na_2SO_4$; all solvent evaporations were carried out in vacuo; and all pnmr (proton nuclear magnetic resonance) spectra were at 60 MHz. The abbreviations DMF, TEA, THF and DMSO are used, respectively, for N,N-dimethylformamide, triethylamine, tetrahydrofuran and dimethylsulfoxide.

EXAMPLE 1

6-alpha-Bromopenicillanic Acid 1,1-Dioxide

To 6,6-dibromopenicillanic acid 1,1-dioxide (117.3 g, 0.3 mole), stirring in a mixture of $H_2O$ (600 mL) and ethyl acetate (400 mL), was added in portions $NaHCO_3$ (75.6 g, 0.9 mole) and then $NaHSO_3$ (37.5 g, 0.36 mole). After stirring 1 hour, the pH was adjusted from 3.7 to 1.5 with concentrated HCl. The aqueous layer was separated and extracted 1×400 mL with fresh ethyl acetate. The combined organic layers were backwashed with brine, dried and evaporated to yield title product as a solid; 72 g (76.7%); m.p. 136°–137°, pnmr/$D_2O$-$NaHCO_3$/delta: 1.48 (s, $CH_3$), 1.62 (s, $CH_3$), 4.28 (s, C.3-H), 5.12 (d, J=1.7, C.6-H), 5.37 (d, J=1.7, C.5-H).

EXAMPLE 2

Benzyl 6-alpha-Bromopenicillanate 1,1-Dioxide

To title product of the preceding Example (24.3 g, 0.0779 mole) in 75 mL DMF was added TEA (7.87 g, 0.0779 mole) and benzyl bromide (13.32 g, 0.0779 mole). The mixture was stirred 16 hours, poured into 250 mL $H_2O$ and extracted 2×200 mL ethyl acetate. The combined organic layers were washed with saturated $NaHCO_3$, $H_2O$ and brine, dried, evaporated to dryness and the residue crystallized from ethyl acetate/hexane; 28.8 g (92%); m.p. 72°–74°; pnmr/$CDCl_3$/delta (ppm): 1.27 (s, $CH_3$), 1.53 (s, $CH_3$), 4.53 (s, C.3H), 4.8 (d, J=1.7, C.6-H), 5.27 (d, J=1.7, C.5-H), 5.3 (d, $CH_2$), 7.5 (s, $C_6H_5$).

Substitution of benzyl bromide with benzhydryl chloride or 2-naphthylmethyl bromide produces the corresponding benzhydryl and 2-naphthylmethyl esters.

EXAMPLE 3

Benzyl 6,6-Dibromopenicillanate 1,1-Dioxide

By the method of the preceding Example, 6,6-dibromopenicillanic acid 1,1-dioxide (39.2 g) was converted to present title product; 37 g (77%); m.p. (crude) 134°–136°, (recrystallized) 146°–148°; pnmr/CDCl$_3$/delta ppm): 1.27 (s, CH$_3$), 1.55 (s, CH$_3$), 4.62 (s, C.3-H), 5.13 (s, C.5-H), 5.3 (d, CH$_2$), 7.46 (s, C$_6$H$_5$).

EXAMPLE 4

Benzyl 6-alpha-(methoxyaminomethyl)penicillanate 1,1-Dioxide

Title product of Example 2 (4.02 g, 0.01 mole) in dry THF (75 mL) was stirred at −75° under N$_2$. Methylmagnesium bromide (2.98M in ether; 3.35 mL, 0.01 mole) was added dropwise over 3 minutes maintaining less than −67°. Formaldehyde O-methyloxime (0.59 g, 0.01 mole) in THF (25 mL) was cooled to −70°, and BF$_3$ etherate (1.42 g, 0.01 mole) added. The resulting solution of complex was added to the above Grignard solution at −70° and the mixture stirred 1 hour at −70° to −76°. Acetic acid (2 mL) was added over 3 minutes and the reaction mixture warmed and evaporated. The residue was distributed in 50 mL H$_2$O and 100 mL ethyl acetate. The aqueous layer was at pH 1.7. The ethyl acetate layer separated, washed with saturated NaHCO$_3$ (75 mL) and then brine, dried and evaporated to a gum (3.58 g). Chromatography on silica gel, eluting with 4:1 CHCl$_3$:ethyl acetate gave purified title product as a gum; 1.88 g; tlc R$_f$ 0.3 (3:1 CHCl$_3$:ethyl acetate); pnmr/CDCl$_3$/delta (ppm) 1.3 (s, CH$_3$), 1.57 (s, CH$_3$), 3.47 (m, NCH$_2$), 3.58 (s, OCH$_3$), 4.0 (m, C.6-H), 4.52 (s, C.3-H), 4.82 (d, J=1.7, C.5-H), 5.33 (d, OCH$_2$), 7.57 (s, C$_6$H$_5$).

In like manner, the benzhydryl and 2-naphthylmethyl esters of Example 2 are converted to the corresponding benzhydryl and 2-naphthylmethyl esters.

EXAMPLE 5

Benzyl 6-beta-Bromo-6-alpha-(Methoxyaminomethyl)penicillanate 1,1-Dioxide

By the method of the preceding Example title product of Example 3 (26.17 g, 0.0544 mole) was converted to present title product (27.7 g of crude), purified by silica gel chromatography using 17:3 CHCl$_3$:ethyl acetate as eluant; 10.7 g (42.5%); m.p. 107°–109°; tlc R$_f$ 0.52 (17:3 CHCl$_3$:ethyl acetate); pnmr (250 MHz)/CDCl$_3$/delta (ppm): 1.28 (s, CH$_3$), 1.59 (s, CH$_3$), 3.54 (s, OCH$_3$), 3.6 (octet, NCH$_2$), 4.54 (s, C3-H), 4.95 (s, C.5-H), 5.26 (q, OCH$_2$), 5.99 (q, NH), 7.39 (s, C$_6$H$_5$).

EXAMPLE 6

Benzyl 6-beta-(Methoxyaminomethyl)penicillanate 1,1-Dioxide

Title product of the preceding Example (26 g, 0.056 mole) and tri(n-butyl)tin hydride (49.6 g, 0.17 mole) were combined in 250 mL benzene and the mixture refluxed gently for 2 hours. The reaction mixture was evaporated and the residue extracted with hexane, and then dissolved in CH$_3$CN. The CH$_3$CN solution was washed with fresh hexane, separated and evaporated to a gum. The gum was chromatographed on silica gel with 4:1 CHCl$_3$:ethyl acetate as eluant to yield present, purified title product as an oil which crystallized on standing; 11.4 g; m.p. 99°–102°; tlc R$_f$ 0.38 (17:3 CHCl$_3$:ethyl acetate); pnmr/CDCl$_3$/delta (ppm): 1.27 (s, CH$_3$), 1.52 (s, CH$_3$), 3.6 (s, OCH$_3$), 3.67 (m, NCH$_2$), 4.55 (s, C.3-H), 4.75 (d, J=4, C.5-H), 5.3 (d, OCH$_2$), 7.53 (s, C$_6$H$_5$).

EXAMPLE 7

Benzyl 6-alpha-(Methoxyaminomethyl)penicillanate 1,1-Dioxide

Title product of the preceding Example (5.73 g, 0.015 mole) was stirred in 125 mL CH$_2$Cl$_2$, 1,5-diazabicyclo[4.3.0]nonene (1.86 g, 0.015 mole) was added, followed after 1 minute of stirring by CH$_3$CO$_2$H (3.6 g, 0.06 mole) and after 2 more minutes of stirring, 100 mL of H$_2$O. The organic layer was separated, washed with 50 mL saturated NaHCO$_3$ and then 50 mL brine, dried and evaporated to yield title product as a gum; 5.35 g; pnmr identical with the chromatographed product of Example 4.

EXAMPLE 8

6-beta-(Methoxyaminomethyl)penicillanic Acid 1,1-Dioxide

Title product of Example 6 (4.0 g, 0.0105 mole) in 110 mL 10:1 THF:H$_2$O was hydrogenated over 3.0 g 10% Pd/C (50% water wet) under 4 atmospheres pressure of H$_2$ for 2 hours, monitoring by tlc. Catalyst was recovered by filtration over diatomaceous earth and THF removed by evaporation. Title product was recovered by filtration of the aqueous residue; 1.7 g; m.p. 196°–198°; ir (KBr) 1778, 1743 cm$^{-1}$.

EXAMPLE 9

Sodium 6-beta-(Methoxyaminomethyl)penicillanate 1,1-Dioxide

Title product was obtained in quantitative yield by dissolving title product of the preceding Example in 10:1 H$_2$O:acetone, adjusting the pH to 7 with one equivalent of NaHCO$_3$ and freeze drying; pnmr/D$_2$O/delta (ppm): 1.43 (s, CH$_3$), 1.57 (s, CH$_3$), 3.55 (s, OCH$_3$), 4.22 (s, C.3-H), 5.0 (d, J=4, C.5-H).

EXAMPLE 10

6-alpha-(Methoxyaminomethyl)penicillanic Acid 1,1-Dioxide

Title product of Examples 4 and 7 (4.7 g, 0.0123 mole) was hydrogenated by the procedure of Example 8. Following recovery of the catalyst, the filtrate was evaporated to yield present title product as a tacky solid; tlc R$_f$ 0.70 (6:1:1 acetone:CH$_3$CO$_2$H:H$_2$O). The entire batch was used in the next Example.

Title product is also obtained by the same hydrogenation procedure from the benzhydryl or 2-naphthylmethyl esters of Example 4.

By the same method title product of Example 16 below is converted to 6-alpha-(ethoxyaminomethyl)-penicillanic acid 1,1-dioxide.

EXAMPLE 11

Sodium 6-alpha-(Methoxyaminomethyl)penicillanate 1,1-Dioxide

By the procedure of Example 9, the entire batch of title product from the preceding Example was converted to present title product; 3.2 g; pnmr/D$_2$O/delta (ppm): 1.43 (s, CH$_3$), 1.57 (s, CH$_3$), 3.42 (m, CH$_2$), 3.53 (s, OCH$_3$), 3.86 (m, C.6-H), 4.2 (s, C.3-H), 4.95 (d, J=1.7, C.5-H); ir (KBr) 1777, 1621 cm$^{-1}$.

EXAMPLE 12

Mixture 6-alpha- and 6-beta-(Methoxyaminomethyl)penicillanic Acid 1,1-Dioxide

Title product of Example 5 (2.0 g, 4.34 mmole) in 5:2 THF:H$_2$O (70 mL) containing NaHCO$_3$ (1 g) was hydrogenated over 2 g 10% Pd/C (50% water wet) under 4 atmospheres pressure of hydrogen for 2 hours. The catalyst was recovered by filtration and THF evaporated from the filtrate. The aqueous residue was adjusted from pH 7.4 to 5.5 with dilute HCl and freeze dried. The residue was chromatographed on silica gel, initially eluting with 9:1 acetone:CH$_3$OH to remove less polar impurities and then with 17:3 acetone:CH$_3$OH to obtain title product as an approximately 1:1 mixture; 220 mg; pnmr (250 MHz)/DMSO-d$_6$ (ppm) includes 1.31, (s, CH$_3$), 1.33 (s, CH$_3$), 1.42 (s, CH$_3$), 1.45 (s, CH$_3$), 3.39 (s, OCH$_3$), 3.41 (s, OCH$_3$), 4.9 (m, C.5-H); ir (KBr) 1785, 1616 cm$^{-1}$; tlc R$_f$0.5 (6:2:1 2-butanone:H$_2$O:CH$_3$CO$_2$H).

By stopping the hydrogenation at an earlier stage, an intermediate mixture of benzyl 6-alpha- and 6-beta-(methoxyaminomethyl)penicillanate 1,1-dioxide is isolated.

EXAMPLE 13

6-alpha-(Aminomethyl)penicillanic Acid 1,1-Dioxide

Title product of Examples 4 and 7 (0.5 g, 0.0013 mole) in 3:1 THF:H$_2$O (20 mL) was hydrogenated over 500 mg of Raney nickel catalyst under 4 atmospheres of hydrogen for 2 hours, monitoring by tlc. The reaction was filtered and filtrate evaporated to yield title product as a white solid identical in all respects with authentic material; pnmr/D$_2$O/delta (ppm): 1.42 (s, CH$_3$), 1.57 (s, CH$_3$), 3.55 (m, CH$_2$), 3.97 (m, C.6-H), 4.22 (s, C.3-H), 4.98 (d, J=1.7, C.5-H); tlc R$_f$ 0.3 (6:1:1 acetone:CH$_3$CO$_2$H:H$_2$O).

By the same method, title product of Example 27 (0.28 g) was converted to the same title product, which was further purified by dissolving in H$_2$O, washing with ethyl acetate, treatment with activated carbon, and evaporation with THF chase; 0.08 g.

EXAMPLE 14

6-beta-(Aminomethyl)penicillanic Acid 1,1-Dioxide

By the method of the preceding Example, title product of Example 6 (130 mg) in 25 mL 3:2 THF:H$_2$O in the presence of 200 mg Raney nickel was converted to present title product; identical with authentic material; tlc R$_f$0.3 (6:1:1 acetone:CH$_3$CO$_2$H:H$_2$O); pnmr/D$_2$O/delta (ppm) includes 1.47 (s, CH$_3$), 1.6 (s, CH$_3$), 3.81 (m, CH$_2$), 4.43 (s, C.3-H), 5.33 (d, J=4, C.5-H).

EXAMPLE 15

Mixture of 6-alpha- and 6-beta-(Aminomethyl)penicillanic Acid 1,1-Dioxide

Title product of Example 5 (110 mg, 0.24 mmole) in 15 ml 2:1 THF:H$_2$O containing NaHCO$_3$ (20 mg, 0.24 mmole) was hydrogenated over 100 mg Raney nickel according to the preceding two Examples to yield present title mixture of products in alpha:beta ratio of about 1:1, showing the tlc R$_f$ and pnmr bands of these products.

EXAMPLE 16

Benzyl 6-alpha-(Ethoxyaminomethyl)penicillanate 1,1-Dioxide

Title product of Example 2 (80.6 g, 0.20 mole) in 800 mL dry THF was cooled to −70°. CH$_3$MgBr (69 mL of 2.9M in ether, 0.20 mole) was added over 40 minutes, maintaining temperature by the rate of addition. Meanwhile, in a separate flask formaldehyde O-ethyloxime (16.3 g, 0.22 mole) and BF$_3$.etherate (31.2 g, 26.9 mL, 0.22 mole) in 100 mL dry THF was cooled to −70°. As soon as CH$_3$MgBr addition was complete, the latter solution was added all at once to the former solution. The temperature, which rose to −60°, was reduced to −70° and the mixture stirred 1 hour. CH$_3$CO$_2$H (28.6 mL, 0.5 mole) was added over 15 minutes, maintaining less than −60°. The mixture was evaporated to a form which was distributed between 700 mL CH$_2$Cl$_2$ and 400 mL H$_2$O and the pH adjusted to 8 with saturated NaHCO$_3$. The resulting emulsion was broken by the addition of ethyl acetate. The organic layer was separated, washed with brine, dried and evaporated to an oil. The oil was chromatographed on a short silica gel column, first eluting less polar impurities with CHCl$_3$ and then eluting crude product with ethyl acetate. The latter was isolated as a second oil, which was rechromatographed on 500 g silica gel eluted with 1:19 ethyl acetate:CHCl$_3$, monitored by tlc. Pure product fractions were combined and evaporated to yield purified title product as an oil, 13.9 g, tlc R$_f$0.4 (4:1 CHCl$_3$:ethyl acetate).

EXAMPLE 17

6-alpha-(Aminomethyl)penicillanic Acid 1,1-Dioxide

By the method of Example 13, title product of the preceding Example (13.9 g) was hydrogenated over Raney nickel. After removing the catalyst by filtration, THF was removed by evaporation and impurities extracted away with ethyl acetate, forming a clean, aqueous solution of title product used directly in the next Example; tlc R$_f$ 0.3 (6:1:1 acetone:CH$_3$CO$_2$H:H$_2$O). Alternatively, title product is isolated by further evaporation or freeze drying to yield product identical to that of Example 13.

EXAMPLE 18

6-alpha-(Benzyloxycarbonylaminomethyl)penicillanic Acid 1,1-Dioxide

Method A

The entire aqueous solution of title product of the preceding Example was diluted with 150 mL THF and stirred at 5°. The pH was adjusted to 8 with 25% NaOH and maintained at 8-8.5 during the 10 minute reaction which followed the addition of benzyl chloroformate (6.05 g, 0.035 mole). THF was removed by evaporation and the aqueous residue extracted with ether. The aqueous layer was covered with ethyl acetate and adjusted to pH 1.5 with 6N HCl. The aqueous layer was extracted with fresh ethyl acetate. The ehtyl acetate layers were combined, dried and evaporated to yield title product; 7.08 g (50.7% over 2 steps); pnmr/CDCl$_3$/TMS 1.40 (3H, s), 1.55 (3H, s), 3.70 (3H, m), 4.31 (1H, s), 4.58 (1H, m), 5.04 (2H, s), 7.24 (5H, s).

Method B

Title product of Example 13 (3.0 g, 11.45 mmoles) was dissolved in 100 mL 1:1 H$_2$O:methanol. The pH was adjusted and maintained at 8.3-8.7 as benzyl chloroformate (1.79 g, 12.59 mmoles) was added dropwise over several minutes. Following a brief period of stirring the pH was adjusted to 6.0 with 1N HCl and THF removed by distillation in vacuo. The aqueous residue was extracted with 30 mL of ethyl acetate and the extract discarded. Fresh ethyl acetate (50 mL) was added and the pH adjusted to 1.8 with 1N HCl. The aqueous layer was extracted with 50 mL fresh ethyl acetate. The combined organic layer and extract was washed 1×50 mL saturated NaCl, dried (Na$_2$SO$_4$) and evaporated in vacuo to yield title product as a foam, 3.7 g, having pnmr identical with that of title product obtained according to Method A immediately above.

Method C

Title mixed product of Example 23 below (2.5 g, 6.38 mmoles) was dissolved in 50 mL CH$_2$Cl$_2$. 1,8-Diazabicyclo[5.4.0]undec-7-ene (1.94 g, 12.8 mmole) and then trimethylsilyl chloride (0.69 g, 6.38 mmole) were added. After stirring 2 minutes, CH$_3$CO$_2$H (1.53 g, 25.5 mmoles) and then 50 mL H$_2$O were added. The pH was adjusted from 4 to 1.5 with dilute HCl and the layers separated. The aqueous layer was extracted with fresh CH$_2$Cl$_2$. The combined organic layers were dried and evaporated to yield title product as a foam, free of 6-beta-isomer by pnmr, which was identical with the product of methods A and B above.

EXAMPLE 19

Pivaloyloxymethyl 6-alpha-(Benzyloxycarbonylaminomethyl)penicillanate 1,1-Dioxide Method A The title product of the preceding Example 6.75 g, 17 mmoles) and N,N-diisopropylethylamine (3.34 mL, 18.7 mmoles) were dissolved in dimethylformamide (50 mL), chloromethyl pivalate (2.72 mL, 18.7 mmoles) were added, and the mixture allowed to stir at ambient temperature for 20 hours. The reaction mixture was diluted with ethyl ether (300 mL), washed with water (2×100 mL), dried (Na$_2$SO$_4$) and evaporated in vacuo to an oil. The oil was dissolved in 100 mL ether, washed 3×50 mL H$_2$O, dried (Na$_2$SO$_4$) and concentrated in vacuo to yield purified title product as a viscous oil, 4.4 g, pnmr/CDCl$_3$/TMS 1.20 (9H, s), 1.34 (3H, s), 1.51 (3H, s), 3.64 (3H, m), 4.31 (1H, s), 4.60 (1H, d), 5.04 (2H, s), 5.71 (2H, q), 7.24 (5H, s).

Method B

Title product of the preceding Example (7.08 g, 0.0179 mole) was stirred in a mixture of 40 mL H$_2$O and 200 mL CHCl$_3$. The pH was adjusted to 8.2 with dilute NaOH, tetrabutylammonium sulfate (6.0 g, 0.017 mole) was added, and the mixture stirred 10 minutes while maintaining the pH at 8. The layers were separated. The aqueous layer was salted and extracted with fresh CHCl$_3$. The organic layers were combined, dried and evaporated to a gum which was dissolved in 100 mL acetone together with chloromethyl pivalate (2.83 g, 0.0187 mole). After stirring 24 hours, the reaction mixture was evaporated and the residue chromatographed on silica gel with gradient elution (CHCl$_3$; 19:1 CHCl$_3$:ethyl acetate; and 9:1 CHCl$_3$:ethyl acetate), monitoring by tlc. In this case the product (6.28 g) solidified; mp 75-82; tlc R$_f$ 0.5 (4:1 CHCl$_3$:ethyl acetate); pnmr as above. Recrystallization from ether increased the mp to 96°-98°.

EXAMPLE 20 p-Toluenesulfonate Salt of Pivaloyloxymethyl 6-alpha-(Aminomethyl)penicillanate 1,1-Dioxide Method A Title product of the preceding Example (1.8 g, 3.53 mmoles) was hydrogenated in a mixture of THF (40 mL) and H$_2$O (20 mL) over 1.8 g of 10% Pd/C in the presence of pyridinium p-toluenesulfonate (1.77 g, 7.06 mmoles) at 4 atmospheres for 1.5 hours. The catalyst was recovered by filtration over diatomaceous earth and the filtrate stripped of THF in vacuo, during which the title product crystallized, 1.2 g, mp 214°-215° C. (dec.); pnmr/DMSO-d$_6$/TMS 1.16 (9H, s), 1.32 (3H, s), 1.48 (3H, s), 2.28 (3H, s), 3.34 (2H, m), 3.82 (1H, m), 4.60 (1H, s), 5.14 (1H, d, J=2 Hz), 5.75 (2H, ABq), 7.23 (4H, ANq).

Anal. Calcd. for C$_{15}$H$_{24}$O$_7$N$_2$S.C$_7$H$_7$SO$_3$H: C, 48.16; H, 5.88; N, 5.11. Found: C, 48.31; H, 6.11; N, 5.08.

Method B

Title product of the preceding Example (5.28 g, 10.35 moles) in 70 mL THF was added to a slurry of 10% Pd/C (2.5 g) which had been prehydrogenated in 70 mL H$_2$O. The mixture was hydrogenated for 30 minutes at 50 psig. After recovery of the catalyst, p-toluenesulfonic acid (2.16 g) in 5 mL of H$_2$O was added to the filtrate and the identical title product recovered by filtration, 4.08 g (71.9%).

Method C

Mixed title product of Example 24 below (2.1 g) was hydrogenated and product isolated according to Method B above, leaving beta-epimer in mother liquor. The yield was 1.02 g, m.p. 215-216; pnmr as for Method A.

EXAMPLE 21

Benzyl 6-beta-Bromo-6-alpha-(ethoxyaminomethyl)penicillanate 1,1-Dioxide

Method A

Title product of Example 3 (27.5 g, 0.057 mole) in 900 mL dry THF was cooled to −75°. CH$_3$MgBr (19 mL of 2.9M in ether, 0.057 mole was added dropwise over 11 minutes, maintaining less than −70°. To this was added a solution of formaldehyde O-ethyloxime (4.2 g, 0.057 mole) and BF$_3$.etherate (8.1 g, 0.057 mole) in 125 ml THF precooled to −75°. After stirring 1 hour at −75°, CH$_3$CO$_2$H (11 mL) was added dropwise and the mixture evaporated and THF chased with ethyl acetate. The residue was distributed between 500 mL each H$_2$O and ethyl acetate and the pH adjusted from 2.8 to 1.5 with 6N HCl. The organic layer was washed with 50 mL fresh H$_2$O. The combined aqueous layers were backwashed with 25 mL ethyl acetate. The combined organic layers were washed 1×50 mL saturated NaHCO$_3$, 1×50 mL H$_2$O and 1×50 mL brine, dried, decolorized with activated carbon, evaporated (25.4 g) and chromatographed on silica gel eluting with 1:19 ethyl acetate:CHCl₃ and monitoring by tlc. Clean product fractions were combined and evaporated to yield title product; 9.7 g (35.9%); pnmr/CDCl₃/TMS 1.1 (t, 3H), 1.27 (s, 3H), 1.55 (s, 3H), 3.62 (m, 2H), 3.85 (q, 2H), 4.62 (s, 1H), 5.08 (s, 1H), 5.32 (d, 2H), 7.52 (s, 5H); tlc $R_f$ 0.64 (4:1 CHCl₃:ethyl acetate).

Method B

Title product of Example 3 (60 g, 0.125 mole) in 400 mL dry THF was cooled to −91°. CH₃MgCl (68.5 mL of 2M in ether, 0.136 mole) was added over 5 minutes, maintaining less than −85° with external liquid N₂ cooling. After stirring at −70° or lower for 45 minutes, formaldehyde O-ethyloxime (10.02 g, 0.137 mole) and then immediately BF₃.etherate (19.5 g, 0.137 mole) were added. After stirring at −70° for 1 hour the reaction was quenched with 24 mL CH₃CO₂H, then diluted with ethyl acetate (650 mL), warmed, washed 3×400 mL H₂O and evaporated to 150 mL. The resulting crystallized title product was recovered by filration; 23.1 g; m.p. 130°-135°; pnmr as above Method A; an X-ray crystal structure analysis confirmed the structure of this product.

EXAMPLE 22

Mixture of 6-alpha- and 6-beta(Aminomethyl)penicillanic Acid 1,1-Dioxide

Title product of the preceding Example (10 g, 0.021 mole) and sodium bicarbonate (2.0 g, 0.024 mole) in 100 mL of methanol was combined with 12 g Raney nickel slurried in 100 mL H₂O and the mixture hydrogenated at 4 atmospheres for 1.5 hours. The reaction was filtered, stripped of methanol, refiltered and the second filtrate evaporated to dryness to yield 5.9 g of title product; alpha:beta ratio about 3:1; contaminated with a small portion of salts; pnmr includes expected peaks for 6-alpha epimer (see Example 13).

When THF was used in place of methanol, the alpha:-beta ratio in the product was closer to 1:1.

EXAMPLE 23

Mixture of 6-alpha- and 6-beta-(Benzyloxy-carbonylaminomethyl)penicillanic Acid 1,1-Dioxide The preceding Example, in methanol and water, was repeated. Following methanol stripping and the second filtration, the aqueous stream was reacted with benzyl chloroformate according to Method A of Example 18 to yield title product; 4.8 g; alpha:beta ratio about 3:1; pnmr includes expected peaks for the 6-alpha-epimer (see Example 18).

EXAMPLE 24

Mixture of Pivaloyloxymethyl 6-alpha-and 6-beta-(Benzyloxycarbonylamino-methyl)penicillanate 1,1-Dioxide Title product of the preceding Example (4.6 g, 0.0116 mole) was stirred with 100 ml CHCL₃ and 25 ml H₂O, and the pH adjusted to 8.2 with dilute NaOH. Maintaining pH 8-8.5 with dilute NaOH, tetrabutyl-ammonium bisulfate (3.94 g, 0.0116 mole) was added and the mixture stirred 5 minutes. The CHCl₃ was separated. The aqueous layer was salted with Na₂SO₄ and extracted with fresh CHCl₃. The CHCl₃ layers were combined, dried and evaporated to yield intermediate tetrabutylammonium salt as a gum. The latter was dissolved in 80 mL acetone. Chloromethyl pivalate (1.75 g, 1.68 mL, 0.016 mole) was added and the mixture stirred 18 hours. Evaporation to dryness and chromatography of the residue on silica gel, eluting impurities with 250 ml CHCl₃ and 400 mL 1:19 ethyl acetate:CHCl₃ and then product with 3:17 ethyl acetate:CHCl₃, monitoring by tlc, gave title product; 2.12 g, tlc $R_f$ 0.5 (4:1 CHCl₃:ethyl acetate) alpha:beta ratio appears greater than 4:1; pnmr shows expected peaks for the alpha epimer (see Example 19). The present product was hydrogenated according to Example 20, Method C, above.

EXAMPLE 25

Benzyl 6-beta-Bromo-6-alpha-(Benzyl-oxyaminomethyl)-penicillanate 1,1-Dioxide

Title product of Example 3 (9.6 g, 0.02 mole) was reacted with methyl magnesium bromide (6.7 mL of 2.98M, 0.02 mole) at −50° C. to −60° over 15 minutes, and then with BF₃. etherate (2.5 ml, 0.02 mole)/formaldehyde O-benzyloxime (2.7 g, 0.02 mole) at −50° according to the method of Example 16. After 30 minutes at −60° and warming to −20° over 20 minutes, the mixture was quenched with 1 ml CH₃CO₂H and stripped of solvent. The residue was taken up in 100 ml each of saturated NaHCO₃ and ethyl acetate and the resulting emulsion broken with NaCl, and the aqueous layer extracted 2×fresh ethyl acetate. The organic layers were combined, back-washed 2×saturated NaHCO₃ and then brine, dried, stripped, and the residue chromatographed on 300 g silica gel with 1:5 ethyl acetate:hexane as eluant and tlc monitoring. Clean product fractions were combined and evaporated to yield title product; 4.31 g tlc $R_f$ 0.28 (3:1 benzene:ethyl acetate); pnmr/CDCl₃/TMS/delta (ppm) 1.22 (s, 3H), 1.52 (s, 3H), 3.53 (m, 2H), 5.05 (s, 2H), 5.27 (s, 2H), 7.47 (s, 10H).

EXAMPLE 26

Benzyl 6-beta-(Benzyloxyamino-methyl)penicillanate 1,1-Dioxide

By the method of Example 6, title product of the preceding Example (3.51 g, 0.0065 mole) was converted to present title product, using 4:1 hexane:ethyl acetate as eluant in chromatography and collecting 50 mL fractions. Fractions 27-31 gave 2.17 g of title product. The purest fractions were 29-31; 0.8 g; tlc $R_f$ 0.08 (3:1 cyclohexane:ethyl acetate).

EXAMPLE 27

Benzyl 6-alpha- (Benzyloxyamino-methyl)penicillanate 1,1-Dioxide

Method A

According to the procedure of Example 7, title product of the preceding Example (0.8 g) was converted to present title product; 0.8 g; tlc $R_f$ 0.5 (3:1 CHCl₃:ethyl acetate); pnmr/CDCl₃/TMS/delta (ppm) 1.27 (s, 3H), 1.53 (s, 3H), 3.33 (m, 2H), 3.93 (m, 1H), 4.5 (s, 1H), 4.75 (s, 2H), 5.27 (s, 2H), 7.45 (s, 5H), 7.48 (s, 5H), Method B According to the procedure of Example 25, using a reaction time of 1 hour at −70° following addition of BF₃/formaldehyde O-benzyloxime, title product of Example 2 (5.8 g, 0.014 mole) was converted to present title product. Following initial stripping of the quenched reaction mixture, the residual oil was dissolved in 100 mL ethyl acetate, washed 2×50 mL saturated NaHCO₃ and 1×50 mL brine, dried and restripped to a second oil, solidified by trituration with CCl₄ and ether to yield crude title product, 2.16 g. The latter was chromatographed on 90 g silica gel eluting with 2:1 cyclohexane:ethyl acetate to yield purified title product, 0.3 g, identical with the product of Method A.

EXAMPLE 28

Pivaloyloxymethyl 6-alpha-Bromopenicillanate 6-alpha-Bromopenicillanic acid (10 g, 0.032 mole) was dissolved in 100 mL $CH_2Cl_2$, combined with 30 mL $H_2O$, and the pH adjusted to 8.3 with 2N NaOH. Tetrabutylammonium bisulfate (10.86 g, 0.032 mole) was added in portions, maintaining pH 8.0 with 2N NaOH. The organic layer was separated, dried and concentrated to yield intermediate tetrabutylammonium salt as an oil. The oil was dissolved in 100 mL acetone, chloromethyl pivalate (5.11 mL, 0.035 mole) added and the mixture stirred 20 hours under $N_2$, then evaporated. The residue was chromatographed on 200 g silica gel, eluting with $CHCl_3$ in 25 mL fractions. Fractions 7–13 were combined and evaporated to yield title product as a crystalline residue; 3.5 g; pnmr/CDCl₃/TMS/delta (ppm): 1.23 (9H, s), 1.43 (3H, s), 1.57 (3H, s), 4.43 (1H, s), 4.68 (1H, d, J=2Hz), 5.14 (1H, d, J=2Hz), 5.83 (2H, q).

EXAMPLE 29

Pivaloyloxymethyl 6-alpha-Bromo-penicillanate 1,1-Dioxide

Method A

Title product of the preceding Example (4.1 g) and m-chloroperbenzoic acid (3 g) are combined in 50 mL ethyl acetate and stirred under $N_2$ for 20 hours, washed in sequence with 3×5 mL saturated $NaHSO_3$, 3×10 mL saturated $NaHCO_3$ and 1×10 mL brine, dried and evaporated to yield title product.

Method B 6-alpha-Bromopenicillanic acid 1,1-dioxide (30 g, 0.096 mole) was dissolved in DMF (100 mL). Triethylamine (9.68 g, 0.096 mole) and chloromethyl pivalate (14.57 g, 0.096 mole) were added and the mixture stirred 1 day, then diluted with 400 mL $H_2O$ and 140 mL ethyl acetate and the pH adjusted from 3.4 to 1.5 with dilute HCl. The aqueous layer was extracted 2×140 mL fresh ethyl acetate. The organic layers were combined, washed 1×100 mL saturated $NaHCO_3$, 1×100 mL $H_2O$ and 1×100 mL brine and evaporated. The residual oil was triturated with hexane, taken up in $CH_2Cl_2$ and re-evaporated to yield title product as a solid; 10.5 g; m.p. 94°–97°; pnmr/CDCl₃/TMS/delta (ppm): 1.25 (s, 9H), 1.45 (s, 3H), 1.62 (s, 3H), 4.57 (s, 1H), 4.85 (d, 1H, J=1.7Hz), 5.3 (d, 1H, J=1.7Hz), 6.0 (q, 2H).

EXAMPLE 30

Pivaloyloxymethyl 6-alpha-(Ethoxy-aminomethyl)penicillanate 1,1-Dioxide

Title product of the preceding Example (5.0 g, 0.0118 mole) in 160 mL THF was cooled to −100° in a liquid $N_2$/ether bath. At the same time, formaldehyde O-ethyloxime (1.1 g, 0.0147 mole) in 100 mL THF was cooled to −75° in separate flask. CH₃MgBr (6.45 mL of 2.28M in ether, 0.0147 mole) was added over 2 minutes to the first solution, as $BF_3$· etherate (1.8 mL, 2.1 g, 0.0147 mole) was added to the second. The second solution was immediately added to the first solution in one portion; the temperature rose to −80°. The reaction mixture was stirred 10 minutes at −90°, 20 minutes at −75° and 40 minutes at −65°, quenched by the addition of 1.6 mL CH₃CO₂H at the latter temperature, warmed and evaporated to an oil which was chased with ethyl acetate. The oil was partitioned between 100 mL ethyl acetate and 50 mL $H_2O$. The organic layer was separated, washed 2×50 mL $H_2O$ and 1×50 mL and evaporated to a 4.8 g residue. The latter was chromatographed on silic agel, eluting with 2:1 hexane:ethyl acetate in 50 mL fractions. Fractions 21–31 were combined and evaporated to yield title product; 0.82 g; pnmr/CDCl₃/TMS/delta (ppm) 1.17 (t, 3H), 1.23 (s, 9H), 1.45 (s, 3H), 1.62 (s, 3H), 3.48 (m, 2 H), 3.87 (q, 2H), 4.1 (m, 1H), 4.51 (s, 1H), 4.83 (d, 1H, J=1.8Hz), 5.98 (q, 2H).

By the same method, title product of the preceding Example is reacted with formaldehyde O-methyloxime to form pivaloyloxymethyl 6-alpha-(methoxyaminomethyl)-penicillanate 1,1-dioxide.

EXAMPLE 31

Pivaloyloxymethyl 6-alpha-(Amino-methyl)penicillanate 1,1-Dioxide

Title product of the preceding Example (0.6 g) was hydrogenated over Raney nickel according to the procedure of Example 13 and present title product isolated according to Example 20, Method B. Yield: 360 mg, identical to the product of Example 20.

EXAMPLE 32

Pivaloyloxymethyl 6,6-Dibromo-penicillanate 1,1-Dioxide

By the procedure of Example 29, Method B, 6,6-dibromopenicillanic acid 1,1-dioxide (98 g, 0.025 mole) was converted to present title product. The initially isolated product was further purified by chromatography on silica gel using 9:1 hexane:ethyl acetate as eluant, providing title product as a gum which solidified on standing; 25 g; pnmr/CDCl₃/TMS/delta (ppm) 1.23 (s, 9H), 1.43 (s, 3H), 1.6 (s, 3H), 4.63 (s, 1H), 5.13 (s, 1H), 5.93 (q, 2H).

EXAMPLE 33

Pivaloyloxymethyl 6-beta-Bromo-6-alpha-(Ethoxyaminomethyl) penicillanate 1,1-Dioxide Title product of the preceding Example (5.05 g, 0.01 mole) was converted to present title product according to the procedure of Example 30, but reacting with CH₃MgBr at −80°, using a reaction time of 1.5 hour at −70° following addition of the further reagents, and using 4:1 hexane:ethyl acetate as the eluant on chromatography; yield 2.5 g; m.p. 60°–70° tlc $R_f$ 0.4 (4:1 CHCl₃:ethyl acetate); pnmr/CDCl₃/TMS/delta (ppm) 1.17 (t, 3H), 1.25 (s, 9H), 1.43 (s, 3H), 1.6 (s, 3H), 3.63 (m, 2H), 3.87 (q, 2H), 4.63 (s, 1H), 5.1 (s, 1H), 5.93 (g, 2H).

By the same procedure, title product of the preceding Example is reacted with formaldehyde O-methyloxime to produce pivaloyloxymethyl 6-beta-bromo-6-alpha-(methoxyaminomethyl) penicillanate 1,1-dioxide.

By the procedure of Example 6, present title product is converted to pivaloyloxymethyl 6-beta-(ethoxyaminomethyl) penicillanate 1,1-dioxide; and thence, by the procedure of Example 7, to title product of Example 30. In like manner, the corresponding methoxy derivative is converted to pivaloyloxymethyl 6-beta-(methoxyaminomethyl) penicillanate 1,1-dioxide and thence to pivaloyloxymethyl 6-alpha-(methoxyaminomethyl) penicillanate 1,1-dioxide.

By the procedure of Example 22, but adjusting the pH to 6.5–7 after Raney nickel addition, present title product is converted to a mixture of pivaloyloxymethyl 6-alpha- and 6-beta- (aminomethyl) penicillanate 1,1-dioxide. If desired, the 6-alpha epimer is isolated as its p-toluenesulfonate salt after stripping away the methanol, according to the procedure of Example 20, Method B.

EXAMPLE 34

Pivaloyloxymethyl 6-beta-Bromo-6-alpha-(Benzyloxyaminomethyl)penicillanate 1,1-Dioxide Title product of Example 32 (5.05 g, 0.10 mole) was converted to present title product according to the procedure of Example 30, but reacting CH$_3$MgBr at $-60°$ to $-50°$, using a reaction time of 1.0 hours at $-70°$ to $-60°$ after addition of the BF$_3$.etherate and formaldehyde O-benzyloxime solution, and initially 9:1 and then 4:1 hexane:ethyl acetate as eluant on chromatography; yield 1.84 g; tlc R$_f$0.4 (4:1 hexane: ethyl acetate); pnmr/CDCl$_3$/TMS/delta (ppm) 1.2 (s, 9H), 1.4 (s, 3H), 1.6 (s, 3H), 3.65 (m, 2H), 4.67 (s, 1H), 4.93 (s, 1H), 5.12 (s, 2H), 5.97 (q, 2H), 7.5 (s, 5H).

By the procedure of Example 6, present title product is converted to pivaloyloxymethyl 6-beta-(benzyloxyaminomethyl)penicillanate 1,1-dioxide; and thence, by the procedure of Example 7, to pivaloyloxymethyl 6-alpha-(benzyloxyaminomethyl)penicillanate 1,1-dioxide. The latter two compounds are hydrolyzed in 5% solution in 1:1 methanol: H$_2$O, maintaining pH 8–8.5 with dilute NaOH over a 6 hour reaction period, to form 6-beta- and 6-alpha-(benzyloxyaminomethyl)-penicillanic acid 1,1-dioxide, respectively. To isolate these products, the pH is adjusted to 7 with dilute HCl, the methanol is removed by evaporation, the aqueous residue is layered with ethyl acetate and the pH lowered to 1.5, and the ethyl acetate layer separated, dried and evaporated to dryness.

EXAMPLE 35

R- and S-1-(Ethoxycarbonyloxy)ethyl 6-alpha-Bromopenicillanate 1,1-Dioxide 6-alpha-Bromopenicillanic acid (31 g) was dissolved in 500 mL CH$_2$Cl$_2$ and diluted with 200 mL H$_2$O. NaHCO$_3$ (9.3 g) was added, followed by the portionwise addition of tetrabutylammonium bisulfate (37.6 g) while maintaining pH 7.5–8.0 with 2N NaOH. The organic layer was separated, washed with brine, dried and evaporated to yield tetrabutylammonium 6-alpha-bromopenicillanate as an oil (57.8 g).

The oil and alpha-chlorodiethyl carbonate (25.3 mL) were dissolved in 500 mL acetone and stirred in the dark under N$_2$ for 36 hours. The reaction mixture was evaporated to a second oil and chromatographed on 1 Kg silica gel, eluting with 1:4 hexane:CHCl$_3$ and collecting 20 mL fractions. Fractions 33–100 were combined and evaporated to yield crude 1-(ethoxycarbonyloxy)ethyl 6-alpha-bromopenicillante as a third oil (41 g).

The latter and m-chloroperbenzoic acid (30 g) were taken into 500 mL ethyl acetate, stirred under N$_2$ for 20 hours, washed in sequence with 3×50 mL, saturated NaHSO$_3$, 3×100 mL saturated NaHCO$_3$ and 1×100 mL brine, dried and evaporated. The resulting residue was chromatographed in 1 Kg fresh silica gel, developed with 3 L of 1:1 hexane:CHCl$_3$ and then eluted with CHCl$_3$ in 25 mL fractions.

Less polar 81–160 were combined and evaporated to a white foam (15.8 g) which crystallized on combining with 50 mL ether and scratching to yield the title product of S-stereochemistry; 5.2 g; m.p. 140°–143°; tlc (1.99 ethyl acetate:CHCl$_3$) R$_f$0.65; pnmr/CDCl$_3$/TMS/delta (ppm): 1.27 (3H, t, J=7Hz), 1.46 (3H, s), 1.55 (3H, s), 1.58 (3H, d, J=5.5Hz), 4.20 (2H, q, J=7Hz), 4.35 (1H, s), 4.65 (1H, d, J=2Hz), 5.09 (1H, d, J=2Hz), 6.67 (1H, q, J=5.5).

Anal. Calcd. for C$_{13}$H$_{18}$O$_8$NSBr: C, 36.45; H, 4.23; N, 3.27. Found: C, 36.47H, 4.30; N, 3.31.

More polar fractions 161–200 were combined and evaporated to a second while foam (4.1 g) which also crystallized on combining with 50 mL ether and scratching to yield the title product of R-stereochemistry; 2.8 g; m.p. 114°–114.5°; tlc (1:9 ethyl acetate:CHCl$_3$) R$_f$ 0.55; pnmr/CDCl$_3$/TMS/delta (ppm): 1.32 (3H, t, J=7Hz), 1.45 (3H, s), 1.59 (3H, d, J=5.5), 1.62 (3H, s), 4.21 (2H, q, J=7Hz), 4.41 (1H, s), 4.63 (1H, d, J=2Hz), 5.11 (1H, d, J=2Hz), 6.77 (1H, q, J=5.5).

Anal. Calcd. for C$_{13}$H$_{18}$O$_8$NSBr: C, 36.45; N, 4.23; N, 3.27. Found: 36.48; H, 4.26; N, 3,28.

By the procedure of Example 30, title products are converted to R- and S-1(ethoxycarbonyloxy)ethyl 6-alpha-(methoxy- or ethoxyaminomethyl)penicillanate 1,1-dioxide. These compounds are in turn converted to R- and S-1-(ethoxycarbonyloxy)ethyl 6-alpha(aminomethyl)penicillanate 1,1-dioxide, respectively, according to the method of Example 22, but with adjustment of the pH to 6.5–7 with dilute HCl if on addition of the Raney nickel the pH exceeds 7. After the hydrogenation is complete, catalyst is removed by filtration and organic solvent removed by evaporation. Product is extracted into ethyl acetate at pH 8.0 and back into water at pH 4.0. The water is evaporated or freeze dried to yield to desired alpha-(aminomethyl)-esters.

PREPARATION 1

Formaldehyde O-Ethyloxime

NaOH (12.2 g) in 25 ml H$_2$O was added ethoxyamine hydrochloride (27 g, 0.279 mole) in 25 ml H$_2$O, maintaining temperature below 25° with an ice-water bath. The mixture was cooled to $-10°$ and 37% HCHO (20.8 mL, 8.32 g of HCHO) added. Title product was distilled from the reaction mixture; 17.4 g (86%); b.p. 35.8°.

PREPARATION 2

Formaldehyde O-Benzyloxime

37% Formaldehyde (11.7 mL) was added to a slurry of benzyloxyamine hydrochloride (25.0 g, 0.156 mole) in 50 mL H$_2$O. NaOH (6.3 g) in 25 mL H$_2$O was then added over 20 minutes. The temperature rose to 40°. After stirring 2 hours, the reaction mixture was extracted 1×100 mL and 2×25 mL of ether. The ether extracts were combined, washed 2×50 mL saturated NaHCO$_3$ and then 2×50 mL brine, dried and evaporated to yield title product as an oil, 20.0 g b.p. 195.5°.

We claim:

1. A compound having the formula

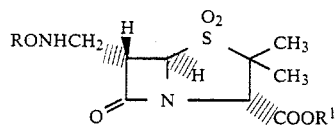

(I)

or

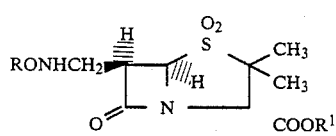

(II)

wherein R is (C$_1$–C$_4$) alkyl or benzyl; and R$^1$ is hydrogen or a conventional ester forming radical which is hydrolyzable under physiological conditions selected from the group consisting of:
  gamma-butyrolacton-4-yl,
  —CHR$^2$OCOR$^3$, or
  —CHR$^2$OCOOR$^3$,
  wherein R$^2$ is hydrogen or methyl and R$^3$ is (C$_1$–C$_6$)alkyl;
or a pharmaceutically acceptable cationic salt thereof when R$^1$ is hydrogen.

2. A compound of claim 1 wherein R$^1$ is hydrogen.
3. A compound of claim 2 having the formula (I).
4. The compound of claim 3 wherein R is methyl.
5. The compound of claim 3 wherein R is ethyl.
6. A compound of claim 2 having the formula (II).
7. The compound of claim 6 wherein R is methyl.
8. The compound of claim 6 wherein R is ethyl.
9. A compound of claim 1 wherein R$^1$ is:
  gamma-butyrolacton-4-yl,
  —CHR$^2$OCOR$^3$, or
  —CHR$^2$OCOOR$^3$,
  wherein R$^2$ is hydrogen or methyl and R$^3$ is (C$_1$–C$_6$)alkyl.
10. A compound of claim 9 of the formula (I) wherein R is methyl or ethyl.
11. A compound of claim 10 wherein R$^1$ is pivaloyloxymethyl.
12. A compound of claim 10 wherein R$^1$ is R- or s-1-(ethoxycarbonyloxy)ethyl.
13. A compound of claim 9 of the formula (II) wherein R$^1$ is pivaloyloxymethyl.
14. The compound of claim 13 wherein R is methyl.
15. The compound of claim 13 wherein R is ethyl.
16. A compound having the formula (III)

(IV)

or (V)

wherein
  R is (C$_1$–C$_4$)alkyl or benzyl;
  R$^4$ is a conventional carboxy protecting group removable by hydrogenolysis selected from the group consisting of:
    benzyl,
    benzhydryl, or
    2-naphthylmethyl; and
  R$^5$ is R$^4$ or a conventional ester forming radical which is hydrolyzable under physiological conditions selected from the group consisting of:
    gamma-butyrolacton-4yl,
    —CHR$^2$OCOR$^3$, or
    —CHR$^2$OCOOR$^3$, wherein R$^2$ is hydrogen or methyl and R$^3$ is (C$_1$–C$_6$)alkyl.

17. A compound of claim 16 of the formula (III) wherein R$^4$ is benzyl.
18. The compound of claim 17 wherein R is methyl.
19. The compound of claim 17 wherein R is ethyl.
20. The compound of claim 17 wherein R is benzyl.
21. A compound of claim 16 of the formula (IV) wherein R$^4$ is benzyl.
22. The compound of claim 21 wherein R is methyl.
23. The compound of claim 21 wherein R is ethyl.
24. The compound of claim 21 wherein R is benzyl.
25. A compound of claim 16 having the formula (V) wherein R is ethyl.
26. The compound of claim 25 wherein R$^5$ is benzyl.
27. The compound of claim 25 wherein R$^5$ is pivaloyloxymethyl.
28. The compound of claim 16 having the formula (V) wherein R is methyl and R$^5$ is benzyl.

* * * * *